US010709973B2

(12) United States Patent
Osawa et al.

(10) Patent No.: US 10,709,973 B2
(45) Date of Patent: Jul. 14, 2020

(54) FRAGRANCE PRESENTATION DEVICE

(71) Applicant: Sony Interactive Entertainment Inc., Tokyo (JP)

(72) Inventors: Hiroshi Osawa, Kanagawa (JP); Shinichi Hirata, Kanagawa (JP); Yoichi Nishimaki, Kanagawa (JP)

(73) Assignee: Sony Interactive Entertainment Inc., Tokyo (JP)

( * ) Notice: Subject to any disclaimer, the term of this patent is extended or adjusted under 35 U.S.C. 154(b) by 26 days.

(21) Appl. No.: 15/570,508

(22) PCT Filed: Jan. 26, 2016

(86) PCT No.: PCT/JP2016/052168
§ 371 (c)(1),
(2) Date: Oct. 30, 2017

(87) PCT Pub. No.: WO2016/199441
PCT Pub. Date: Dec. 15, 2016

(65) Prior Publication Data
US 2018/0147484 A1    May 31, 2018

(30) Foreign Application Priority Data
Jun. 12, 2015    (JP) ................................. 2015-119718

(51) Int. Cl.
*A63F 13/25* (2014.01)
*G06F 3/01* (2006.01)
(Continued)

(52) U.S. Cl.
CPC ................ *A63F 13/25* (2014.09); *A61L 9/12* (2013.01); *A61L 9/122* (2013.01); *A61L 9/125* (2013.01);
(Continued)

(58) Field of Classification Search
CPC . A63F 13/25; A63F 13/50; A61L 9/12; A61L 9/122; A61L 9/125; A61L 9/16; G06F 3/01; H04N 5/64
See application file for complete search history.

(56) References Cited

U.S. PATENT DOCUMENTS 4,952,024 A     8/1990  Gale
5,565,148 A  *  10/1996 Pendergrass, Jr. ...... A61L 9/122
                                                          261/30
(Continued)

FOREIGN PATENT DOCUMENTS

CN    101389359 A    3/2009
CN    101528274 A    9/2009
(Continued)

OTHER PUBLICATIONS

English translation of WO2013005615 (Year: 2013).*
(Continued)

*Primary Examiner* — Regina M Yoo
(74) *Attorney, Agent, or Firm* — Matthew B. Dernier, Esq.

(57) ABSTRACT

The object of the present invention is to provide a fragrance presentation device which prevents an unintended smell from being presented. A fragrance presentation device for use with a display device which can be mounted on the head of a user includes a fragrance presentation module disposed in a fragrance presentation position in the vicinity of the nostrils of a person on which the display device is mounted, a fragrance holder having a fragrance container for holding a fragrance therein, the fragrance holder placing the fragrance container in a position spaced from the fragrance presentation position at least while the fragrance is not presented, and delivering the fragrance out of the fragrance container when the fragrance in the fragrance container is presented, and a fragrance conductor for conducting the
(Continued)

fragrance which has been delivered out of the fragrance holder to the fragrance presentation module.

6 Claims, 4 Drawing Sheets

(51) Int. Cl.
    *H04N 5/64*      (2006.01)
    *A61L 9/12*      (2006.01)
    *A63F 13/50*      (2014.01)
    *A61L 9/16*      (2006.01)

(52) U.S. Cl.
    CPC ............... *A61L 9/16* (2013.01); *A63F 13/50* (2014.09); *G06F 3/01* (2013.01); *H04N 5/64* (2013.01); *A63F 2250/021* (2013.01); *A63F 2300/308* (2013.01)

(56) References Cited

U.S. PATENT DOCUMENTS

| | | | |
|---|---|---|---|
| 5,610,674 A * | 3/1997 | Martin | B01F 3/022 352/85 |
| 6,390,453 B1 * | 5/2002 | Frederickson | A61M 15/02 261/100 |
| 6,672,129 B1 | 1/2004 | Frederickson et al. | |
| 6,783,084 B1 * | 8/2004 | Nelson | A61L 9/125 239/304 |
| 6,803,987 B2 * | 10/2004 | Manne | A61L 9/122 352/85 |
| 7,154,579 B2 * | 12/2006 | Selander | A61L 9/125 352/85 |
| 7,419,535 B2 * | 9/2008 | Malle | A61L 9/14 261/26 |
| 7,734,159 B2 | 6/2010 | Beland | |
| 8,032,014 B2 | 10/2011 | Cheung | |
| 8,295,529 B2 * | 10/2012 | Petersen | H04R 1/083 381/371 |
| 9,931,425 B2 * | 4/2018 | Edwards | A61L 9/032 |
| 2002/0018181 A1 * | 2/2002 | Manne | A61L 9/122 352/85 |
| 2005/0212151 A1 * | 9/2005 | Malle | A61L 9/122 261/30 |
| 2008/0085103 A1 | 4/2008 | Beland | |
| 2009/0261181 A1 | 10/2009 | Cheung | |
| 2012/0325941 A1 | 12/2012 | Nakamoto | |
| 2015/0048178 A1 * | 2/2015 | Edwards | A61L 9/032 239/13 |
| 2015/0241708 A1 | 8/2015 | Watanabe | |

FOREIGN PATENT DOCUMENTS

| | | |
|---|---|---|
| JP | 2007079620 A | 3/2007 |
| JP | 2014-39694 A | 3/2014 |
| WO | 2013005615 A1 | 1/2013 |
| WO | 2015025511 A1 | 2/2015 |

OTHER PUBLICATIONS

Net: "Development of an aroma generating device and research and development of an aroma presentation method based on an olfactory model", Ken'ichi Okada and two others, [online], [retrieved May 10, 2015], 56 pages, Internet URL: http://www.soumu.go.jp/main_sosiki/joho_tsusin/scope/event/h22yokousyu/session/uc1(pre).pdf.
International Preliminary Report on Patentability and Written Opinion for corresponding PCT Application No. PCT/JP2016/052168, 11 pages, dated Dec. 21, 2017.
Notification of Reason for Refusal for corresponding JP Application No. 2017-523122, 12 pages, dated Jul. 10, 2018.
International Search Report for corresponding PCT Application No. PCT/JP2016/052168, 4 pages, dated Apr. 5, 2016.
Notification of Reason for Refusal for corresponding JP Application No. 2017-523122, 12 pages, dated Mar. 12, 2019.
First Office Action for corresponding CN Application No. 201680032870A, 19 pages, dated Aug. 27, 2019.

\* cited by examiner

FRAGRANCE PRESENTATION DEVICE

TECHNICAL FIELD

The present invention relates to a fragrance presentation device that presents smells to the user.

BACKGROUND ART

Heretofore, there has existed, as a device for presenting smells, a device of the desktop type for ejecting pulses of fragrances that make the user feel smells or a device of the type that is hung from the neck of the user (NPL 1). There has also been developed a mask-type device to be attached to a display for being mounted on the head of the user (head-mount display) which has been in widespread use in recent years.

CITATION LIST

Non Patent Literature

[NPL 1] inet: "Development of an aroma generating device and research and development of an aroma presentation method based on an olfactory model", Ken'ichi Okada and two others, [online], [retrieved May 10, 2015], Internet URL: http://www.soumu.go.jp/main_sosiki/joho_t-susin/scope/event/h22yokousyu/session/uc1(pre).pdf

SUMMARY

Technical Problem

Generally, the above device for presenting smells includes a plurality of containers installed in position for storing therein substances (fragrances) from which to produce smells. The fragrances are gradually released from the containers. However, the mask-type device or the like, which is placed in the vicinity of the nostrils through which the user feels smells, is problematic in that it tends to present unintended smells with fragrances that have leaked from the containers.

The conventional devices are designed in terms of the presentation of smells for a certain period of time at a certain intensity level, but have not taken into account a situation in which a smell that has been presented thus far is to be removed and another smell is to be presented, such as when an image displayed on a head-mount display changes scenes, for example.

The present invention has been made under the above circumstances, and it is an object of the present invention to provide a fragrance presentation device which prevents an unintended smell from being presented and which is capable of dealing with switching between smells to be presented.

Solution to Problem

In order to solve the conventional problems described above, there is provided in accordance with the present invention a fragrance presentation device for use with a display device which can be mounted on the head of a user, including a fragrance presentation module disposed in a fragrance presentation position in the vicinity of the nostrils of a person on which the display device is mounted, a fragrance holder having a fragrance container for holding a fragrance therein, the fragrance holder placing the fragrance container in a position spaced from the fragrance presentation position at least while the fragrance is not presented, and delivering the fragrance out of the fragrance container when the fragrance in the fragrance container is presented, and a fragrance conductor for conducting the fragrance which has been delivered out of the fragrance holder to the fragrance presentation module.

Advantageous Effect of Invention

According to the present invention, an unintended smell is prevented from being presented. According to the present invention which is provided with the fragrance removal module, switching between smells to be presented is dealt with.

DESCRIPTION OF EMBODIMENTS

Figure 1:
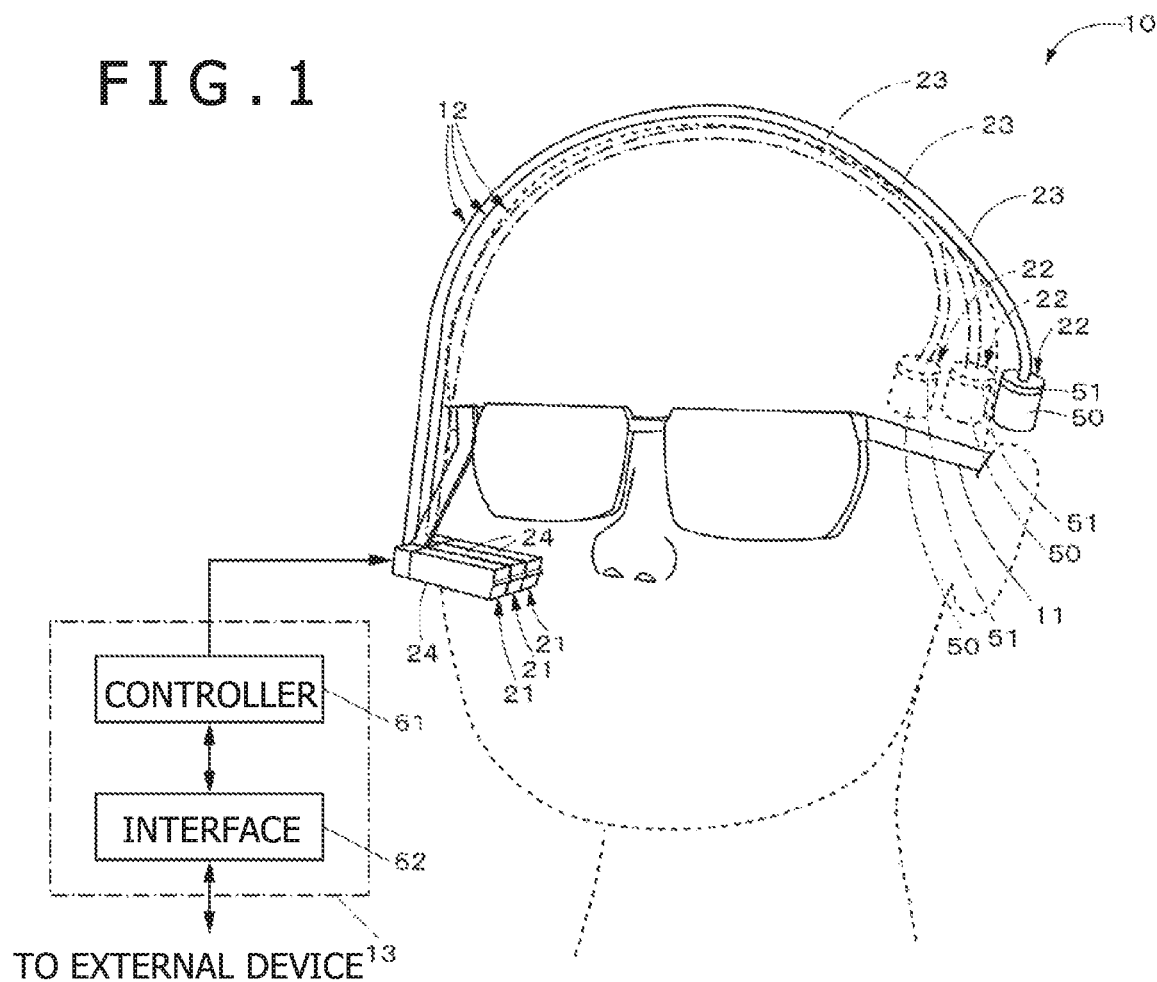
FIG. 1 is a schematic view depicting by way of example a fragrance presentation device according to an embodiment of the present invention.

An embodiment of the present invention will be described below with reference to the drawings. As depicted in FIG. 1, a fragrance presentation device 10 according to the present embodiment is used with a display device 11 that can be mounted on the head of the user (head-mount display, hereinafter referred to as "HMD"), and mounted on the head of the user. The fragrance presentation device 10 includes a plurality of fragrance presentation bodies 12 and a control unit 13. The fragrance presentation bodies 12 and the control unit 13 may be individually connected to each other (in a star topology around the control unit 13), or the control unit 13 may be connected to the fragrance presentation bodies 12 through a common bus, or the fragrance presentation bodies 12 may be connected in a daisy chain topology. If the fragrance presentation bodies 12 are connected through the bus or in the daisy chain topology, then any of widely known methods, such as a method using address information, etc. may be used as a method for the control unit 13 to designate a fragrance presentation body 12 to be instructed. Therefore, such a method will not be described below.

Figure 2:
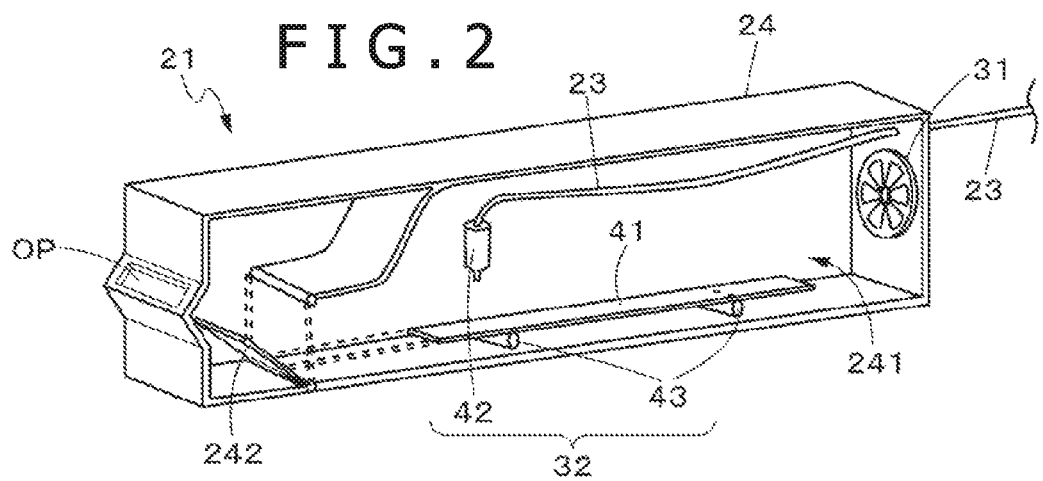
FIG. 2 is a view depicting by way of example structural details of the inside of a presentation body container of the fragrance presentation device according to the embodiment.

As depicted in FIG. 1, the fragrance presentation bodies 12 are shaped as a quadratic prism each, and are arranged in a single array or a plurality of arrays. Alternatively, the fragrance presentation bodies 12 may be shaped as a hexagonal prism each, and may be arranged in a honeycomb pattern. According to the present embodiment, as depicted in FIG. 2, each of the fragrance presentation bodies 12 includes a fragrance presentation module 21, a fragrance holder 22, a fragrance conductor 23, and a presentation body container 24. The fragrance presentation module 21 is disposed in a fragrance presentation position in the vicinity of the nostrils of the user. The fragrance conductor 23 serves to conduct a fragrance delivered out of the fragrance holder 22 to the fragrance presentation module 21. It should be noted that FIG. 1 depicts an example in which the fragrance holder 22 is disposed at the rear side of the head of the user. According to the present embodiment, the fragrance is of a fluid form, and the fragrance conductor 23 includes a flexible tube, for example, whose diameter, etc. are determined for allowing the fragrance to flow therethrough.

As depicted in FIG. 2, the presentation body container 24 is shaped as a hollow quadratic prism and has an opening OP defined in at least one longitudinal end face thereof. The presentation body container 24 defines therein a storage chamber 241 in the shape of a quadratic prism which stores the fragrance presentation module 21 therein. In FIG. 2, one side of the presentation body container 24 is illustrated as broken away in order to indicate the inside of the presentation body container 24.

As depicted in FIG. 2, the fragrance presentation module 21 includes a fan 31 and a fragrance presenter 32. The fan 31 has one side exposed to ambient air, and is capable of rotating in a normal direction (in a direction to draw in ambient air and generate an air flow toward the nostrils of the user on which the fragrance presentation device 10 according to the present embodiment is mounted), and of reversing (in a direction to draw in air from the nostrils of the user on which the fragrance presentation device 10 according to the present embodiment is mounted and generate an air flow to be discharged into the ambient air). A filter containing a deodorant for adsorbing fragrances may be disposed on the ambient air side of the fan 31.

The fragrance presenter 32 includes a carrier 41, a dropper 42, and a carrier mover 43. The carrier 41 carries a fragrance supplied from the fragrance conductor 23. The dropper 42 drops a fragrance onto the carrier 41 when it is turned on under external control. The carrier mover 43 moves the carrier 41 under external control. The fragrance presenter 32 presents a fragrance on an air flow that is generated by the fan 31 in operation.

The carrier 41 of the fragrance presenter 32 is shaped as a column or a slender flat plate. The carrier 41 is made of a film, a nonwoven fabric, or the like which holds a fragrance that has been dropped onto it and gradually releases the fragrance held thereby (i.e., has a sustained fragrance release capability). The carrier 41 is fixed to the carrier mover 43 to be described later. In accordance with an instruction input from the control unit 13, the dropper 42 drops an instructed amount of fragrance onto the carrier 41 by way of an acoustic or heating action. The dropper 42 may include something similar to a head used in an ink jet printer, for example.

The carrier mover 43 includes a linear actuator, for example, and moves the carrier 41 in the presentation body container 24 between a first position in which the carrier 41 is stored in the storage chamber 241 and a second position in which the carrier 41 projects from the storage chamber 241 in accordance with an instruction input from the control unit 13.

The fragrance holder 22 has a container receptacle 51 that receives a fragrance container 50 storing a fragrance therein. The container receptacle 51 is connected to one end of the fragrance conductor 23, and introduces the fragrance in the fragrance container 50 that has been received into the fragrance conductor 23. According to the present embodiment, the fragrances are of a fluid form, and any of various existing mechanisms may be used as a mechanism for introducing such a fluid substance into the fragrance conductor 23. Therefore, such a mechanism will not be described in detail below.

According to the present embodiment, the fragrance holder 22 is spaced from the fragrance presentation module 21. The fragrance holder 22 may be disposed in a place from which the fragrance is unlikely to reach the nostrils of the user even if it leaks at the position of the fragrance holder 22, e.g., may be disposed in a position behind an ear of the user (at the back of the head). Providing the fragrance is made up of components lighter than air, the fragrance holder 22 may not be disposed at the back of the head insofar as the fragrance holder 22 is disposed in a position higher than the nostrils.

The control unit 13 includes a controller 61 and an interface 62. The controller 61 includes a microcomputer or the like, and is provided with a program executor such as a central processing unit (CPU) or the like and a memory for holding programs to be executed by the program executor. The controller 61 performs a predetermined processing sequence in response to an externally input instruction via the interface 62. Specifically, according to the present embodiment, the controller 61 receives, as an externally input instruction, information that specifies a fragrance presentation body 12 (information that specifies a fragrance to be presented) and an instruction for presenting the fragrance or stopping presenting the fragrance, and controls the fragrance presentation body 12 specified by the received instruction to present the fragrance or stop presenting the fragrance according to the instruction.

For presenting the fragrance, the controller 61 controls the dropper 42 of the specified fragrance presentation module 21 to drop the fragrance onto the carrier 41. The controller 61 also operates the fan 31 of the fragrance presentation module 21 to generate an air flow for transporting the fragrance carried by the carrier 41 toward the nostrils of the user. The controller 61 further controls the carrier mover 43 to move the carrier 41 to the position in which the carrier 41 projects from the storage chamber 241 within the presentation body container 24.

The fragrance carried by the carrier 41 is transported by the air flow generated by the fan 31 and released from the opening of the presentation body container 24, make it possible for the user to feel the smell of the fragrance.

For stopping presenting the fragrance, the controller 61 reverses the fan 31 of the specified fragrance presentation module 21 to generate an air flow from the nostrils of the user toward the fan 31 of the fragrance presentation module 21. Since the air generated by the fan 31 removes the fragrance from the vicinity of the nostrils of the user and releases the fragrance into ambient air, the user stops feeling the smell of the fragrance in a relatively short period of time.

The controller 61 may de-energize the fans 31 of fragrance presentation modules 21 which have not been instructed to present fragrances or to stop presenting fragrances. The controller 61 may also de-energize the fan 31 when a predetermined period of time has passed after it has stopped presenting the fragrance.

The fragrance presentation module 21 has a shutter 242 on the side of the storage chamber 241 from which the carrier 41 can project. When the shutter 242 is closed, the storage chamber 241 is blocked from outside. The shutter 242 can be opened and closed by the control unit 13. The control unit 13 opens the shutter 242 when it rotates the fan 31 in the normal direction or reverses the fan 31, and closes the shutter 242 when it de-energizes the fan 31. Consequently, when there is no instruction to present the fragrance and the fan 31 is de-energized, the possibility that the fragrance will leak from the storage chamber 241 is lowered, and the user will not be presented with the unintended smell.

The interface 62, which includes a serial interface such as a universal serial bus (USB) or the like, for example, outputs an externally input instruction to the controller 61.

According to the present embodiment, the fragrance presentation device 10 may further include a casing that houses the fragrance presentation module 21 of at least the fragrance presentation body 12, among the fragrance presentation body 12 and the control unit 13, the casing being shaped to cover at least the nostrils of the user when the fragrance presentation device 10 is mounted on the head of the user. If the fragrance presentation device 10 includes the casing, then the casing is shaped to create a space of a predetermined shape in the vicinity of the nostrils, and the fragrance presentation module 21 is disposed in the space. In addition, if the fragrance presentation device 10 includes the casing, then it may further include a ventilator for replacing the air in the space with ambient air. The casing has an opening in its portion that defines the space in the vicinity of the nostrils, the opening being held in fluid communication with ambient air. The opening may be provided with a filter, which may include a deodorant.

The fragrance presentation device 10 according to the present embodiment is basically of the structure described above, and operates as follows: In use, the fragrance presentation device 10 according to the present embodiment is connected to a game machine for home use, for example. In the example below, it is assumed that the fragrance presentation device 10 includes three fragrance presentation bodies 12, and fragrance containers 50 that store respective fragrances A, B, and C for making the user feel different smells are set in the fragrance holders 22 of the fragrance presentation bodies 12. It is also assumed that the controllers 61 of the fragrance presentation bodies 12 have received settings indicating which fragrance containers 50 are set in which fragrance presentation bodies 12 or have detected which fragrance containers 50 are set in which fragrance presentation bodies 12. For making such detection, integrated circuit (IC) tags that provide information specifying the fragrances in the fragrance containers 50 may be applied to the fragrance containers 50, for example, and the information may be detected by reading the IC tags.

Figure 3:
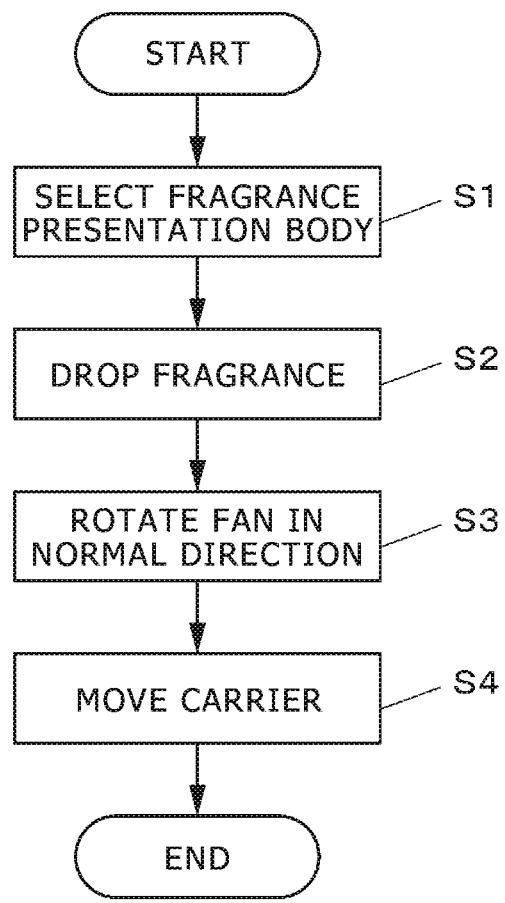
FIG. 3 is a flowchart depicting by way of example an operation sequence of fragrance presentation by the fragrance presentation device according to the embodiment.

When the fragrance presentation device 10 receives information specifying a fragrance to be presented (information specifying either one of the fragrances A, B, and C) and an instruction to present the fragrance from the game machine for home use, the fragrance presentation device 10 starts a processing sequence depicted in FIG. 3. The fragrance presentation device 10 selects one of the fragrance presentation bodies 12 in which the fragrance container 50 storing the fragrance specified by the received information has been set (S1). The fragrance presentation device 10 then controls the dropper 42 of the fragrance presentation module 21 of the selected fragrance presentation body 12 to drop the fragrance onto the carrier 41 (S2). At this time, the fragrance is supplied from the fragrance holder 22 through the fragrance conductor 23.

The fragrance presentation device 10 rotates in the normal direction the fan 31 of the fragrance presentation module 21 of the fragrance presentation body 12 selected in step S1 (S3), generating an air flow for transporting the fragrance carried by the carrier 41 toward the nostrils of the user. The fragrance presentation device 10 controls the carrier mover 43 of the fragrance presentation body 12 selected in step S1 to move the carrier 41 to the position in which the carrier 41 projects from the storage chamber 241 in the presentation body container 24 (to move the carrier 41 to the position indicated by the broken lines in FIG. 2: S4). At this time, if the storage chamber 241 is provided with the shutter 242, then the fragrance presentation device 10 opens the shutter of the fragrance presentation body 12 selected in step S1.

In this manner, the fragrance specified by the instruction from the game machine for home use is released from the fragrance presentation device 10, making it possible for the user to feel the smell of the fragrance.

Figure 4:
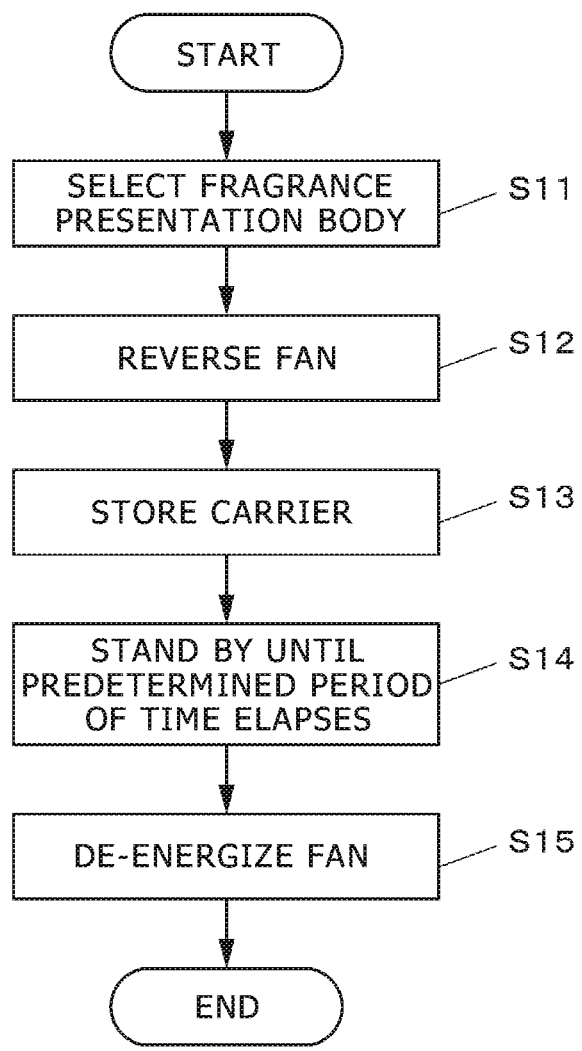
FIG. 4 is a flowchart depicting by way of example an operation sequence of fragrance removal by the fragrance presentation device according to the embodiment.

For removing the fragrance that has been presented thus far quickly from the vicinity of the nostrils of the user, as when a game being played changes scenes, for example, the game machine for home use outputs information specifying a fragrance that has been instructed to be presented (information specifying either one of the fragrances A, B, and C) and an instruction to stop presenting the fragrance, to the fragrance presentation device 10. In response to the instruction, the fragrance presentation device 10 starts a processing sequence depicted in FIG. 4. The fragrance presentation device 10 selects one of the fragrance presentation bodies 12 in which the fragrance container 50 storing the fragrance specified by the received information has been set (S11).

The fragrance presentation device 10 reverses the fan 31 of the fragrance presentation module 21 of the fragrance presentation body 12 selected in step S1 (S12), generating an air flow for transporting the fragrance from the nostrils of the user toward the fan 31 of the fragrance presentation module 21. The fragrance presentation device 10 controls the carrier mover 43 of the fragrance presentation body 12 selected in step S1 to move the carrier 41 to the position in which the carrier 41 is stored in the storage chamber 241 (S13). At this time, if the storage chamber 241 is provided with the shutter 242, then the fragrance presentation device 10 keeps open the shutter 242 of the fragrance presentation body 12 selected in step S11.

Subsequently, the fragrance presentation device 10 stands by until a predetermined period of time elapses (S14). When predetermined period of time has elapsed, the fragrance presentation device 10 de-energizes the fan 31 of the fragrance presentation module 21 of the fragrance presentation body 12 selected in step S1 (S15). At this time, if the storage chamber 241 is provided with the shutter 242, then the fragrance presentation device 10 closes the shutter.

Intensity of Smell

According to the present embodiment, the fragrance presentation device 10 may receive an instruction about the intensity of a smell to be presented, included in the instruction to present the smell, and may present the smell having the intensity based on the received information.

In the present example, the controller 61 controls the intensity of the smell by controlling at least one of the following:

(1) the rotational speed of the fan 31 (air volume);
(2) the dropped amount of the fragrance from the dropper 42; and
(3) how much the carrier 41 is to project from the storage chamber 241.

According to a specific example, the controller 61 receives the information about the intensity of a smell to be presented as a value P in a range of 0 to Pmax (Pmax>0). Providing the carrier mover 43 is able to control the amount Q by which the carrier 41 projects from the storage chamber 241 in a range of 0 to Qmax (Qmax>0), the controller 61 calculates the amount Q by which the carrier 41 projects from the storage chamber 241 according to $Q=(Qmax/Pmax)*P$. Then, the controller 61 instructs the carrier mover 43 to move the carrier 41 to project from the storage chamber 241 by the amount Q. In this fashion, it is possible to change the amount by which the fragrance is dispersed, presenting the intensity of the smell.

Environmental Aroma

In the description thus far, when there is an instruction to present a fragrance, the controller controls the fragrance presentation device to present the fragrance specified by the instruction. The present embodiment is not limited to such a fragrance presentation. In the absence of an instruction to present a fragrance (or in response to an instruction to finish presenting a fragrance), the controller may control the fragrance presentation device to present a particular fragrance (a fragrance for making the user feel the smell of a surrounding environment, or an environmental aroma, hereinafter referred to as "environmental fragrance").

Specifically, in the absence of an instruction to present a fragrance (or in response to an instruction to finish presenting a fragrance), the controller 61 selects a fragrance presentation body 12 in which an environmental fragrance determined in advance as a fragrance to be presented in the absence of an instruction has been set.

Then, the controller 61 has the fragrance presentation device 10 control the dropper 42 of the fragrance presentation module 21 of the selected fragrance presentation body 12 to drop the environmental fragrance onto the carrier 41. The controller 61 rotates in the normal direction the fan 31 of the fragrance presentation module 21, generating an air flow for transporting the environmental fragrance carried by the carrier 41 toward the nostrils of the user, and controls the carrier mover 43 of the fragrance presentation body 12 to move the carrier 41 to the position in which the carrier 41 projects from the storage chamber 241 within the presentation body container 24. At this time, if the storage chamber 241 is provided with the shutter 242, then the fragrance presentation device 10 opens the shutter of the selected fragrance presentation body 12.

When the controller 61 receives an instruction to present a fragrance other than the environmental fragrance, the controller 61 reverses the fan 31 of the fragrance presentation module 21 of the fragrance presentation body 12 in which the environmental fragrance has been set, generating an air flow from the nostrils of the user toward the fan 31 of the fragrance presentation module 21, and also controls the carrier mover 43 of the same fragrance presentation body 12 to move the carrier 41 to the position in which the carrier 41 is stored in the storage chamber 241. When the carrier 41 is stored in the storage chamber 241, the controller 61 de-energizes the fan 31 of the fragrance presentation module 21 of the fragrance presentation body 12, and closes the shutter 242. Then, the controller 61 controls the fragrance presentation device 10 to present the fragrance, specified by the instruction, other than the environmental fragrance (carries out the processing sequence depicted in FIG. 3).

Deodorization

According to the present embodiment, the plural fragrance presentation bodies 12 may include one in which no fragrance container 50 has been set. The fragrance presentation body 12 in which no fragrance container 50 has been set can be used with a view to removing the fragrance from the vicinity of the nostrils of the user. The fragrance presentation body 12 in which no fragrance container 50 has been set realizes a fragrance removal module according to the present invention. Specifically, in response to an instruction to remove the fragrance released thus far, rather than information that specifies a fragrance presentation body 12 (information that specifies a fragrance, etc.), the controller 61 stops presenting fragrances from all the fragrance presentation bodies 12 in which the fragrance containers 50 have been set (by controlling the carrier mover 43 of the fragrance presentation body 12 to move the carrier 41 to the position in which the carrier 41 is stored in the storage chamber 241, and de-energizing the fan 31 or de-energizing the fan 31 after reversing it), and reverses the fan 31 of the fragrance presentation body 12 in which no fragrance container 50 has been set, generating an air flow from the nostrils of the user toward the fan 31. At this time, if the storage chamber 241 is provided with the shutter 242, then the controller 61 opens the shutter 242 of the fragrance presentation body 12 in which no fragrance container 50 has been set.

According to this example of the present embodiment, since the fragrance is removed from the vicinity of the nostrils of the user and released into the ambient air by the air flow generated by the fan 31, the user becomes unable to feel the smell of the fragrance in a relatively short period of time, and hence the fragrance that has been presented thus far can quickly be removed when the smell to be presented is changed at the time the image displayed on the HMD 11 changes scenes.

According to the present embodiment, furthermore, the controller 61 may control either one of the fragrance presentation bodies 12 in which the fragrance containers 50 have been set to present a fragrance, reverse the fan 31 of one of the fragrance presentation bodies 12 which has not presented a fragrance (which may be a fragrance presentation body 12 with no fragrance container 50 set therein), and control the rotational speed of the fan 31 (air volume), thereby controlling the intensity of the smell. In this example, while a smell is being presented, the fragrance that presents the smell is removed to make it possible to perform fine control over the intensity of the smell.

According to another example of the present embodiment, the plural fragrance presentation bodies 12 may include one in which a fragrance container 50 storing a deodorizing fragrance (so-called a masking agent or a pairing agent) has been set. In this example, the fragrance presentation body 12 in which a fragrance container 50 storing such a deodorizing fragrance has been set (hereinafter referred to as "deodorizing fragrance presentation body") may be used for the purpose of removing another fragrance (other than the deodorizing fragrance) from the vicinity of the nostrils of the user or preventing the user from feeling another fragrance (other than the deodorizing fragrance). In this example, the fragrance presentation body 12 in which the fragrance container 50 storing the deodorizing fragrance has been set realizes a fragrance removal module according to the present invention.

According to this example, specifically, in response to an instruction to remove the fragrance released thus far, rather than information that specifies a fragrance presentation body 12 (information that specifies a fragrance, etc.), the controller 61 stops presenting fragrances from all the fragrance presentation bodies 12 in which the fragrance containers 50 storing fragrances other than the deodorizing fragrance have been set (by controlling the carrier mover 43 of the fragrance presentation body 12 to move the carrier 41 to the position in which the carrier 41 is stored in the storage chamber 241, and de-energizing the fan 31 or de-energizing the fan 31 after reversing it), and also controls the dropper 42 of the fragrance presentation module 21 of the deodorizing fragrance presentation body to drop the deodorizing fragrance supplied instead of a fragrance from the fragrance holder 22 through the fragrance conductor 23 onto the carrier 41.

The controller 61 rotates in the normal direction the fan 31 of the fragrance presentation module 21 of the deodorizing fragrance presentation body, generating an air flow for transporting the deodorizing fragrance carried by the carrier 41 toward the nostrils of the user, and controls the carrier mover 43 of the deodorizing fragrance presentation body to move the carrier 41 to the position in which the carrier 41 projects from the storage chamber 241 within the presentation body container 24. At this time, if the storage chamber 241 is provided with the shutter 242, then the controller 61 opens the shutter 242 of the deodorizing fragrance presentation body. In this example, as the deodorizing fragrance is released in the vicinity of the nostrils of the user, the smell of the fragrance is deodorized. Specifically, if the deodorizing fragrance is a so-called masking agent, the aroma of the deodorizing fragrance makes the user less liable to feel the smell of other fragrances (fragrances other than the deodorizing fragrance). If the deodorizing fragrance is a so-called pairing agent, the deodorizing fragrance chemically reacts with other fragrances (fragrances other than the deodorizing fragrance) and is reduced to other aromatic substances (or odorless substances), so that the user will not feel the smell of other fragrances (fragrances other than the deodorizing fragrance).

Therefore, the example of the present embodiment employs deodorizing methods of (1) reversing the fan 31 to remove the fragrance from the vicinity of the nostrils of the user, (2) preventing the fragrance released from the fragrance carrier 41 from leaking toward the nostrils of the user with the shutter 242 provided on the storage chamber 241, and (3) masking or pairing with the released fragrance with the deodorizing fragrance. These deodorizing methods may be used in any desired combinations.

Another Example of Carrier

Figure 5:
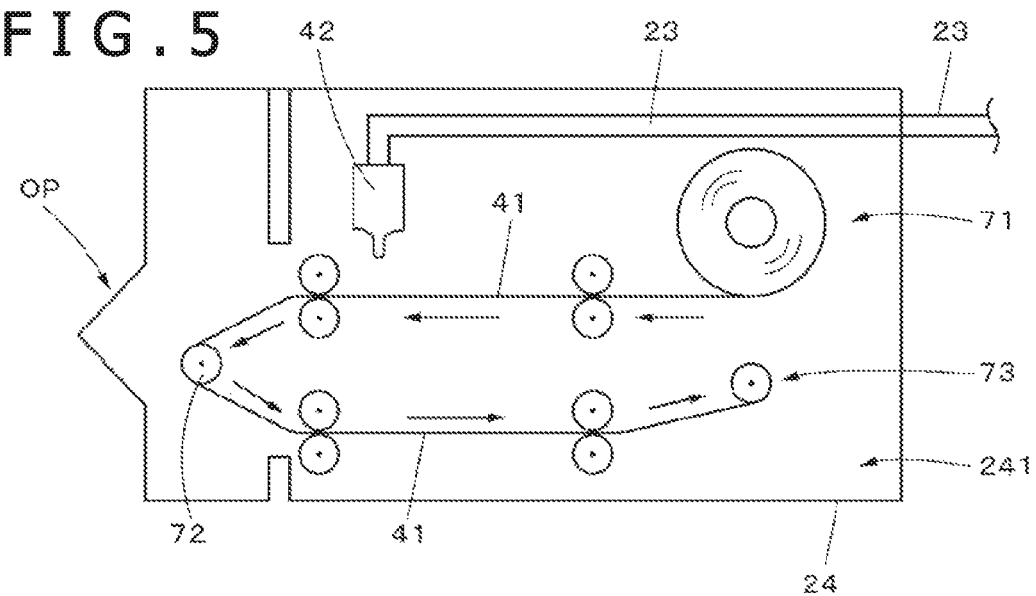
FIG. 5 is a view depicting by way of example another fragrance presentation module for the fragrance presentation device according to the embodiment.

The carrier 41 illustrated in the above example may be replaced with a carrier 41 in the form of a sheet that can be continuously supplied which is wound on a supply roller 71 disposed in the storage chamber 241, as depicted in FIG. 5. In this example, the carrier mover 43 pulls the carrier 41 from the supply roller 71 via a roller 72 disposed outside of the storage chamber 241 and winds the carrier 41 around a take-up roller 73 in the storage chamber 241.

In this example, the controller 61 controls the dropper 42 to drop the fragrance onto a portion of the carrier 41. When the controller 61 gives an instruction to project the carrier 41 from the storage chamber 241, the carrier mover 43 transports the portion of the carrier 41 onto which the fragrance has been dropped to the position of the roller 72. For stopping presenting the fragrance, the controller 61 controls the carrier mover 43 to transport the portion of the carrier 41 onto which the fragrance has been dropped to the position of the take-up roller 73. At this time, the take-up roller 73 winds the carrier 41 without the fragrance being newly dropped onto the carrier 41, so that a portion of the carrier 41 onto which no fragrance has been dropped is positioned at the roller 72, thereby stopping presenting the fragrance.

According to the present embodiment, the carrier 41 and the dropper 42 may not be employed, but another means for gradually releasing the fragrance, e.g., a shutter whose amount of opening is controllable, may be disposed at the end of the fragrance conductor 23 near the fragrance presentation module 21, and the controller 61 may control the amount of opening of the shutter for releasing the fragrance.

Example of Left and Right Fragrance Presentation Modules

According to another example of the present embodiment, a pair of left and right fragrance presentation modules 21 may be disposed in association with the respective left and right nostrils of the user. The paired fragrance presentation modules 21 may be supplied with a fragrance from the same fragrance holder 22 through corresponding fragrance conductors 23. The left and right fragrance presentation modules 21 which present the same fragrance may separately be controlled by the controller 61 for presenting the fragrance or stopping presenting the fragrance.

In this example, in response to information specifying a fragrance to be presented and information about the location of the fragrance (information representing from which of left and right positions the smell is to come) which are supplied from an external source, the controller 61 may control, based on the information about the location, the amount of the fragrance to be released from each of the paired fragrance presentation modules 21 which present the fragrance specified by the information.

Warm Air/Cool Air

According to the present embodiment, each of the fragrance presentation modules 21 may have a cool warm unit for heating or cooling the air flow. The cool warm unit may include a Peltier device or the like. In this example, the controller 61 may receive information specifying a fragrance to be presented and information about the temperature at which to present the fragrant, which are supplied from an external source, and control the cool warm unit of the fragrance presentation module 21 corresponding to the fragrance to be presented, on the basis of the information (or the information and an ambient air temperature corresponding to the fragrance to be presented), for heating or cooling the air flow.

Each of the fragrance presentation modules 21 may have a humidifier for humidifying the air flow. In this example, the controller 61 may receive information specifying a fragrance to be presented and an instruction for humidifying the air flow at the time the fragrance is to be presented, which are supplied from an external source, and control the humidifier of the fragrance presentation module 21 corresponding to the fragrance to be presented, on the basis of the instruction, for humidifying the air flow.

Example in which Fragrance Presentation Modules are Moved

According to the present invention, each of the fragrance presentation modules 21 may be placed in a fragrance presentation position (in a prescribed range in the vicinity of the nostrils of the user) at the time it presents a fragrance. Each of the fragrance presentation modules 21 may be provided with a guide rail disposed between the fragrance presentation position and a retracted position spaced from the nostrils (e.g., the back of the head of the user). Those fragrance presentation modules 21 which present fragrances that have not been instructed to be presented are moved to their retracted positions. In response to an instruction to present a fragrance, the controller 61 may move the fragrance presentation module 21 in which the fragrance to be presented has been set along the guide rail to the fragrance presentation position, and control the fragrance presentation module 21 to present the fragrance (in steps S1 through S4 depicted in FIG. 3).

The fragrance presentation position is in the prescribed range in the vicinity of the nostrils of the user. A range in which a fragrance dispersed when the fan 31 is rotated in the normal direction reaches the nostrils may be experimentally determined as the prescribed range with respect to the facial features of the average user.

In accordance with an externally input instruction, the controller 61 may control the fragrance presentation module 21 to present a fragrance by controlling where it is to be positioned within the prescribed range, or may control the fragrance presentation module 21 to present a fragrance while controlling how it is to move within the prescribed range (in a time-dependent mode of motion which represents which speed the fragrance presentation module 21 is to move at and which positions the fragrance presentation module 21 is to move from and to).

If the paired left and right fragrance presentation modules 21 that present the same fragrance are provided, then the fragrance presentation position of the fragrance presentation module 21 disposed on the right side of the user may lie within a prescribed range at the right of the position of the right nostril of the user, and the fragrance presentation position of the fragrance presentation module 21 disposed on the left side of the user may lie within a prescribed range at the left of the position of the left nostril of the user.

With the above arrangement, furthermore, when there is an instruction to stop the presentation of a fragrance, the controller 61 selects the fragrance presentation body 12 in which the fragrance container 50 containing the fragrance specified by the received information has been set, and reverses the fan 31 of the fragrance presentation module 21 of the selected fragrance presentation body 12, generating an air flow from the nostrils of the user toward the fan 31 of the fragrance presentation module 21. The controller 61 also controls the carrier mover 43 of the fragrance presentation body 12 to move the carrier 41 to the position in which the carrier 41 is stored in the storage chamber 241. At this time, if the storage chamber 241 is provided with the shutter 242, then the fragrance presentation device 10 keeps open the shutter 242 of the fragrance presentation body 12 selected in step S11. The controller 61 moves the fragrance presentation module 21 to the retracted position, thereby spacing the fragrance presentation module 21 from the vicinity of the nostrils of the user. Thereafter, the controller 61 de-energizes the fan 31 of the fragrance presentation module 21. If the storage chamber 241 is provided with the shutter 242, then the fragrance presentation device 10 closes the shutter.

Example in which a Fragrance Presentation Module and a Fragrance Holder are Integrally Combined Together In case the fragrance presentation module 21 is movable between the fragrance presentation position and the retracted position, the fragrance holder 22 may not necessarily be spaced from the fragrance presentation module 21. In other words, the fragrance holder 22 and the fragrance presentation module 21 may be integrally formed with each other. In this case, as described above, each of the fragrance presentation modules 21 may be provided with a guide rail disposed between the fragrance presentation position and the retracted position spaced from the nostrils (e.g., the back of the head of the user). Those fragrance presentation modules 21 which present fragrances that have not been instructed to be presented are moved to their retracted positions. In response to an instruction to present a fragrance, the controller 61 may move the fragrance presentation module 21 in which the fragrance to be presented has been set along the guide rail to the fragrance presentation position, and control the fragrance presentation module 21 to present the fragrance. In this example, when the fragrance in the fragrance holder 22 is used up, the fragrance presentation module 21 and the fragrance holder 22 may be replaced as an integral entity.

The fragrance presentation module may have a fan capable of reversing the direction of air delivered thereby and a fragrance presenter for presenting a fragrance on an air flow generated by the fan.

The fragrance presenter may have a carrier for carrying a fragrance supplied from the fragrance conductor, a carrier storage chamber for storing the carrier, and a carrier mover for moving the carrier between a position in which the carrier projects from the carrier storage chamber and a position in which the carrier is stored in the carrier storage chamber.

The fragrance presenter may also have a shutter for closing the carrier storage chamber when the carrier is in the position in which the carrier is stored in the carrier storage chamber. The fragrance presentation device may further have a fragrance removal module disposed in the vicinity of the nostrils of the person on which the display device is mounted, for removing the fragrance from the vicinity of the nostrils. The fragrance removal module may be provided with a fan for generating an air flow from the vicinity of the nostrils in a direction away from the nostrils. The fragrance removal module may remove the fragrance by presenting a deodorizing fragrance.

REFERENCE SIGNS LIST

10 Fragrance presentation device, 12 Fragrance presentation body, 13 Control unit, 21 Fragrance presentation module, 22 Fragrance holder, 23 Fragrance conductor, 24 Presentation body container, 31 Fan, 32 Fragrance presenter, 41 Carrier, 42 Dropper, 43 Carrier mover, 50 Fragrance container, 51 Container receptacle, 61 Controller, 62 Interface, 71 Supply roller, 72 Roller, 73 Take-up roller, 241 Storage chamber, 242 Shutter

The invention claimed is:

1. A fragrance presentation device, comprising:
   a fragrance presentation module having a mounting element for connecting to a head-mounted display device, where the mounting element places the fragrance presentation module in a vicinity of nostrils of a person when said head-mounted display device is mounted on the head of the person;
   a fragrance holder having a fragrance container for holding a fragrance therein, said fragrance holder placing said fragrance container in a position spaced away from the nostrils of the person;
   a fragrance conductor for conducting the fragrance out of the fragrance container of the fragrance holder to said fragrance presentation module; and
   a fragrance presenter for presenting the fragrance into an air flow, where said fragrance presenter includes: (i) a carrier for carrying the fragrance supplied from said fragrance conductor, (ii) a carrier storage chamber for storing said carrier, and (iii) a carrier mover for moving said carrier between a position in which said carrier projects from said carrier storage chamber and a position in which said carrier is stored in said carrier storage chamber,
   wherein the fragrance presentation module is controllable such that the fragrance conducted by the fragrance conductor may be regulated.

2. The fragrance presentation device according to claim 1, wherein said fragrance presentation module includes a fan capable of reversing direction of air delivered thereby, and the fragrance presenter presents the fragrance into the air flow.

3. The fragrance presentation device according to claim 1, wherein said fragrance presenter further includes
   a shutter for closing the carrier storage chamber when said carrier is in the position in which said carrier is stored in said carrier storage chamber.

4. The fragrance presentation device according to claim 1, further comprising:
   a fragrance removal module disposed in the vicinity of the nostrils of the person on which said head-mounted display device is mounted, for removing the fragrance from the vicinity of the nostrils.

5. The fragrance presentation device according to claim 4, wherein said fragrance removal module is provided with a fan for generating an air flow from the vicinity of the nostrils in a direction away from the nostrils.

6. The fragrance presentation device according to claim 4, wherein said fragrance removal module removes the fragrance by presenting a deodorizing fragrance.

* * * * *